United States Patent

Ramamurthy et al.

[11] Patent Number: 5,871,447
[45] Date of Patent: Feb. 16, 1999

[54] DOPPLER ENERGY-RELATED PARAMETERS IN AN ULTRASOUND IMAGING SYSTEM

[75] Inventors: Bhaskar S. Ramamurthy, Santa Clara, Calif.; George R. Sutherland, Linköoping, Sweden

[73] Assignee: Acuson Corporation, Moutain View, Calif.

[21] Appl. No.: 744,384

[22] Filed: Nov. 7, 1996

[51] Int. Cl.⁶ .......................................... A61B 8/00
[52] U.S. Cl. ........................................ 600/443; 600/453
[58] Field of Search ....................... 367/135; 128/661.09, 128/661.01, 661.06; 73/861.25

[56] References Cited

U.S. PATENT DOCUMENTS

| | | | |
|---|---|---|---|
| 4,928,698 | 5/1990 | Bonnefous | 600/455 |
| 5,014,710 | 5/1991 | Maslak et al. | 367/135 |
| 5,243,987 | 9/1993 | Shiba | 600/463 |
| 5,285,788 | 2/1994 | Arenson et al. | 600/491 |
| 5,471,990 | 12/1995 | Thirsk | 600/455 |
| 5,474,073 | 12/1995 | Schwartz et al. | 73/861.25 |
| 5,553,621 | 9/1996 | Otterson | 600/453 |
| 5,555,534 | 9/1996 | Maslak et al. | 367/135 |
| 5,622,172 | 4/1997 | Li et al. | 600/443 |
| 5,676,148 | 10/1997 | Koo et al. | 1/1 |

FOREIGN PATENT DOCUMENTS 3-277351  12/1991  Japan .

OTHER PUBLICATIONS

Bonnefous et al., "Time Domain Formulation of Pulse–Doppler Ultrasound and Blood Velocity Estimation by Cross Correlation," *Ultrasonic Imaging B*, 73–85 (1986).

*Primary Examiner*—Marvin M. Lateef
*Assistant Examiner*—Maulin Patel
*Attorney, Agent, or Firm*—Morrison & Foerster

[57] ABSTRACT

A method and apparatus for ultrasound imaging of Doppler energy-related parameters is described. An ultrasound imaging system includes a transducer for transmitting an ultrasound signal into a body and receiving a reflected ultrasound signal. The system determines the energy of the reflected signal from tissue within the body. Signal processing circuitry determines a Doppler intensity spectrum of the signal reflected from the tissue. The Doppler spectrum represents energy of the tissue-reflected signal as a function of Doppler frequency and time. Integration circuitry integrates the Doppler spectrum over Doppler frequency to determine the energy of the tissue-reflected signal as a function of time for display in strip mode. The system also determines an energy-velocity product. The integration circuitry may comprise circuitry for raising the Doppler intensity spectrum to a power m to generate a first spectral function and for raising a velocity-related function to a power n to generate a first velocity function. The integration circuitry integrates the product of the first spectral function and the first velocity function to determine the energy-velocity product function as a function of time.

34 Claims, 5 Drawing Sheets

DOPPLER ENERGY-RELATED PARAMETERS IN AN ULTRASOUND IMAGING SYSTEM

BACKGROUND OF THE INVENTION

In B-mode medical ultrasound imaging, an ultrasound scanner transmits an ultrasound signal into a patient and detects the intensity of the signal reflected from different depths. The scanner thus provides an image of structures within the body. Conventional Doppler imaging goes one step further and detects the velocity of moving tissues and fluids in the direction of the transmitted ultrasound signal. The conventional Doppler ultrasound machine employs two imaging modalities for measuring velocity: color flow imaging and strip Doppler imaging. Ultrasound scanners typically implement strip Doppler imaging in one of three different modes: PW or pulse wave imaging, HPRF or high pulse repetition frequency imaging, and CW or continuous wave imaging. According to the pulse Doppler technique, the ultrasound scanner places a range gate over the region of interest, and interrogates the region with multiple ultrasound pulses. The scanner samples the returning echoes and determines velocities using the Doppler principle. The velocity of the target is calculated and displayed based upon the sampled echoes.

HPRF imaging is similar to PW imaging. The difference is that the imaging system places and receives echoes from multiple range gates within the body. In HPRF mode, echoes from prior transmissions reflected from deep structures within the body are received at the same time as echoes from shallow structures. The system samples the composite echo from all range gates, and displays the frequency spectrum (converted to velocity scale) of the composite echo.

In continuous Doppler imaging, the scanner transmits and receives continuous ultrasound signals to and from the body. The scanner calculates the Doppler frequency spectrum according to continuous-time techniques.

All three strip Doppler imaging modes employ the same display mechanism. The Doppler frequency spectrum is plotted along the ordinate against time along the abscissa. In practice, the frequency axis is converted into a velocity axis using the Doppler equation. Velocity of the target toward and away from the transducer is displayed along the positive and negative halves of the ordinate, respectively. The system modulates the brightness of the pixels in each frequency bin to display the energy of that bin.

In addition to displaying the Doppler frequency spectrum graphically, the ultrasound system typically converts the Doppler frequency information to audio signals. The system distinguishes between the velocity of the target toward and away from the transducer by sending it to different speakers.

Variance is an inherent attribute of all velocity estimates obtained from a Doppler system. The width of the Doppler spectrum is one measure of variance. The spectral width obtained using any of the methods outlined above is due to one or more of many factors, including flow characteristics, signal bandwidth, transit time effects and variance in parameter estimates.

The sensitivity of the Doppler method in measuring the velocity of the target is best if the velocity is parallel to the ultrasound propagation direction. The velocity estimates tend to have a large variance if the angle between the propagation direction and the velocity is larger than sixty degrees. In those situations, velocity estimates are not good indicators of the presence of flow.

Further, the amount of flow is not readily apparent from the conventional strip display mechanism discussed above.

As an example, if there are two plug flows that are identical in velocity and different in flow volume, this difference would be difficult to perceive, especially if the difference in volume is small. In that instance, both flows would cause the same frequency or velocity band to be bright and the resulting small difference in brightness would be the only indication of the difference between the two flows.

Audio processing of Doppler information also has the same disadvantages listed above. If the velocity estimates experience a wide variance, the audio output will be noisy. Furthermore, the strength of the audio output is no indication of the amount of flow in conventional systems.

To overcome these problems, some ultrasound systems employ Doppler techniques to measure reflected energy or power. For example, U.S. Pat. No. 5,243,987, issued to Shiba, describes an ultrasound system for measuring the backscattering power of blood. Shiba employs high pass filtering and thresholding to eliminate reflections from slow-moving structures, such as tissue. The Shiba system displays the intensity of the echo signal by varying the brightness of a gray scale image or the hue of a color display, or as a three dimensional plot of Doppler spectrum against frequency and time. U.S. Pat. No. 5,285,788, issued to Arenson, and assigned to the assignee of the present invention, provides a Doppler tissue imaging (DTI) system that produces a color Doppler image of moving tissue representing estimates of velocity and reflected energy.

U.S. Pat. No. 5,014,710, issued to Maslak, and assigned to the assignee of the present invention, describes a color Doppler imaging system that processes Doppler-shifted echoes into blood flow information, including velocity, variance and power. Further, U.S. patent application Ser. No. 08/691, 204, entitled "Imaging Modality Showing Energy and Velocity," and assigned to the assignee of the present invention, discloses a color Doppler imaging system having a mixed mode in which luminance is a function of the product of the velocity and the energy of the echo signal. All of the patents, applications and other references discussed herein are incorporated by reference herein.

One disadvantage of color display techniques is that the display frame rate is relatively slow with respect to the cardiac cycle. Further, because of the relatively low number of samples used to compute Doppler shift, color systems exhibit a relatively poor signal-to-noise ratio.

The present invention overcomes these disadvantages by providing more flexibility in the diagnostic parameters available in ultrasound machines implementing other display modes.

Further, the invention has potential advantages over another imaging technique—integrated backscatter imaging. This imaging technique is generally used for estimating the echo-density over a region of integration. B-mode information is integrated over a region and displayed instead of the usual echo intensity. The principle behind this technique is the assumption that the energy reflected from a region is related to the density of the reflecting medium at that location. A corollary mode currently exists whereby the integrated backscatter information can be obtained via Doppler processing through the use of Doppler tissue imaging (DTI) in the energy mode.

SUMMARY OF THE INVENTION

The present invention provides a method and apparatus for calculating Doppler energy-related parameters in an ultrasound imaging system. An ultrasound imaging system includes a transducer for transmitting an ultrasound signal into a body and receiving a reflected ultrasound signal. The system determines the energy of the reflected signal from structures, such as tissue, within the body. Signal processing circuitry determines a Doppler squared magnitude (intensity) spectrum of the signal reflected from the structures. The Doppler spectrum represents energy of the tissue-reflected signal as a function of Doppler frequency and time. Integration circuitry integrates the Doppler spectrum over Doppler frequency to determine the energy of the tissue-reflected signal as a function of time for display in strip mode.

Alternatively, the energy may be calculated in the time domain by employing squaring circuitry to determine the squared amplitude of the tissue-reflected signal. Integration circuitry integrates the squared amplitude in the time-domain.

The present invention also determines an energy-velocity product. The integration circuitry frequency-integrates the product of the Doppler squared magnitude spectrum and a velocity-related function to determine the energy-velocity product as a function of time for display in strip mode. The velocity-related function is a function of the Doppler frequency. The integration circuitry may comprise circuitry for raising the Doppler squared magnitude spectrum to a power m to generate a first spectral function and for raising the velocity-related function to a power n to generate a first velocity function. The integration circuitry integrates the product of the first spectral function and the first velocity function to determine the energy-velocity product function as a function of time. In one embodiment, m may be set to 1−n, where m and n are less than 1. The values of m and n may be set by a user.

The system may also include a filter for filtering out spectral components reflected from tissue, and a thresholding circuit for eliminating spectral components having an intensity above an upper threshold intensity so as to eliminate spectral components from tissue. Further, the system may include thresholding circuitry for eliminating spectral components having an intensity below a low threshold intensity so as to eliminate spectral components from blood.

The system may further include audio processing circuitry for processing an audio output related to Doppler frequency. Tone generation circuitry generates a tone related to an energy-related parameter, i.e., energy or energy-velocity. Combining circuitry combines the tone with the audio output. In one embodiment, the tone generation circuitry modulates the frequency of the tone based upon the energy-related parameter. In another embodiment, the tone generation circuitry modulates the amplitude of the tone based upon the energy-related parameter. In both embodiments, the combining circuitry adds the tone to the audio output.

In yet another embodiment, the audio processing circuitry may comprise gain control circuitry for controlling the gain of the audio output in response to the energy-related parameter.

NOTATION AND NOMENCLATURE

While the term "velocity" is used in this application, it should be understood that the velocity can be derived from the Doppler frequency shift by use of the well-known Doppler equation:

$$v = f_d c / 2 f_o \cos\theta$$

where $f_d$ is the Doppler frequency shift, c is the speed of sound in the medium, $f_o$ is the transmitted frequency, and $\theta$ is the Doppler angle (the angle subtended by the ultrasound beam and the direction of flow). Because of the relationships among velocity, frequency, and wavelength, the term "velocity-related function" or "velocity-related parameter" as used in this application, will refer to velocity, frequency, or wavelength. Similarly, because of the well-known relationships among energy, power, and amplitude, the term "energy-related function" or "energy-related parameter" will refer to energy, power, or amplitude. The terms "energy-related function" or "energy-related parameter" will also refer to the energy-velocity product function discussed below. Further, those skilled in the art will recognize that the term "circuitry" as used herein may refer not only to hardware, but to software and other implementations as well.

DETAILED DESCRIPTION OF THE INVENTION

The present invention provides a method and apparatus for obtaining Doppler energy-related parameters in an ultrasound imaging system. In the following description, numerous details are set forth in order to enable a thorough understanding of the present invention. However, it will be understood by those of ordinary skill in the art that these specific details are not required in order to practice the invention. Further, well-known elements, devices, process steps and the like are not set forth in detail in order to avoid obscuring the present invention.

Figure 1:
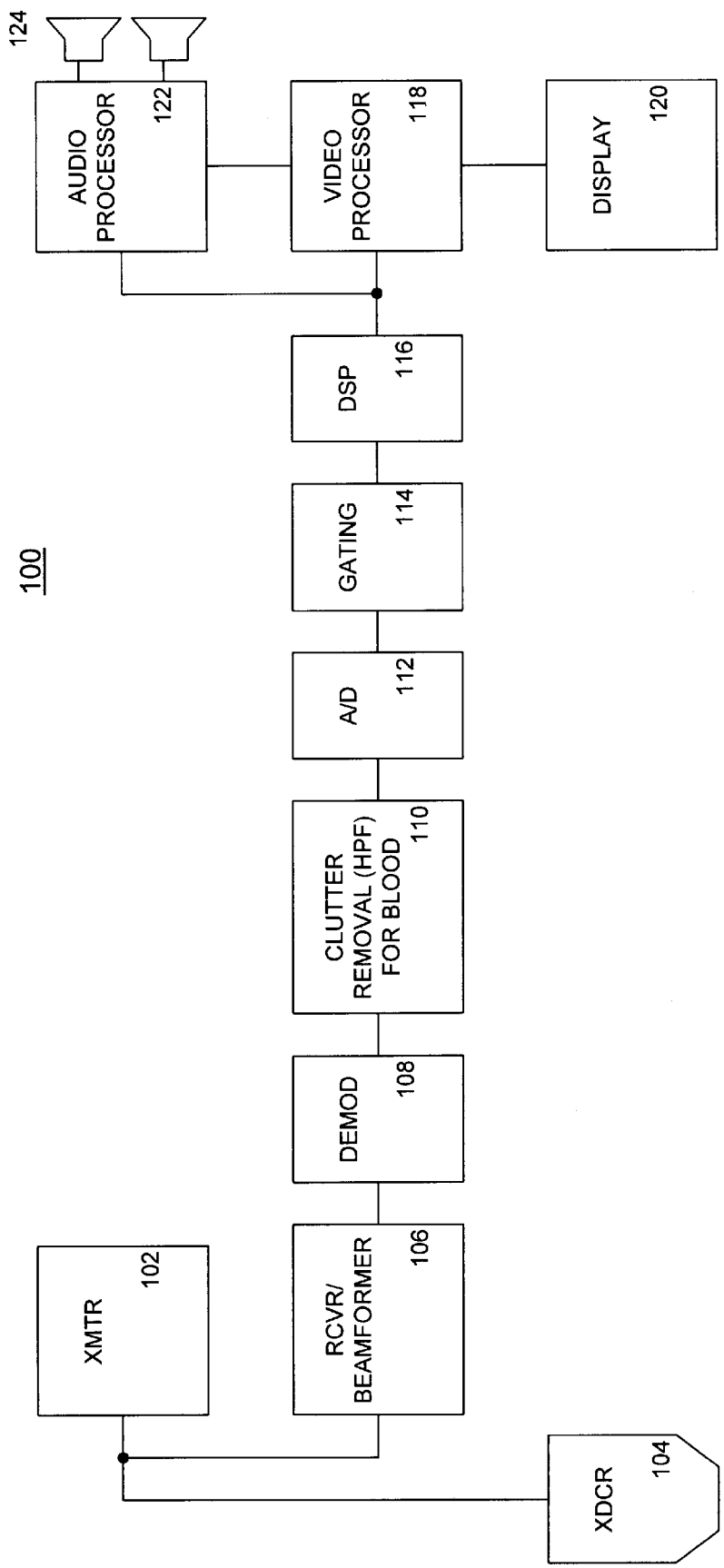
FIG. 1 is a block diagram illustrating an ultrasound system for implementing the present invention.

FIG. 1 is a block diagram illustrating an ultrasound system 100 for implementing the present invention. A transmitter 102 excites an acoustic transducer 104, which propagates ultrasonic energy bursts into a body. The transducer 104 typically comprises a phased array of ultrasound transducer elements. The transducer 104 converts returning ultrasound signals into electrical signals. A receiver/beamformer 106 amplifies and focuses the electrical signals. A quadrature demodulator 108 downshifts the frequency of the focused echo signal by the transducer frequency in order to extract the Doppler frequency shift separated into in-phase and quadrature components. Those skilled in the art will recognize that the signal path may include a high pass clutter removal filter 110 for any Doppler imaging mode for imaging blood. As is known in the art, the location of the clutter filter depends upon the design employed.

An analog-to-digital converter (A/D) 112 digitizes the analog demodulated signals. Gating circuitry 114 (for PW and HPRF modes) gates the digitized output so that only samples from the region of interest are passed on to digital signal processing (DSP) circuitry 116. A range gate integrator in the gating circuitry integrates the demodulated sampled echoes arising within each gate to obtain an integrated echo sample for each gate, as is well known in the art. Such integration reduces the effects of noise. The resulting integrated echo samples are passed on to the DSP circuitry 116 for calculation of the frequency spectrum. For example, 128 consecutive integrated echo samples received from the same gate location may be used to obtain the Doppler spectrum at one point in space.

According to the present invention, the DSP circuitry 116 processes the sampled demodulated signals to derive energy-related parameters and conventional velocity-related parameters. These parameters are, in turn, passed to a video processor 118, which converts the Doppler information to a raster format for a conventional video display 120. The video processor 118 of the present invention converts the information to strip Doppler format in which the energy-related parameter is plotted against the time axis.

The DSP 116 also passes the demodulated signals to the audio processing circuitry 122, which combines these signals and separates the forward and reverse components of the flow that represent motion of the reflectors toward and away from the transducer, as is well known in the art. Each component is sent to one of two speakers 124.

The DSP 116 also passes signals to the audio processor that are proportional to the energy-related parameters. These signals are combined with the conventional signals in the audio processor in a manner described below.

Figure 2:
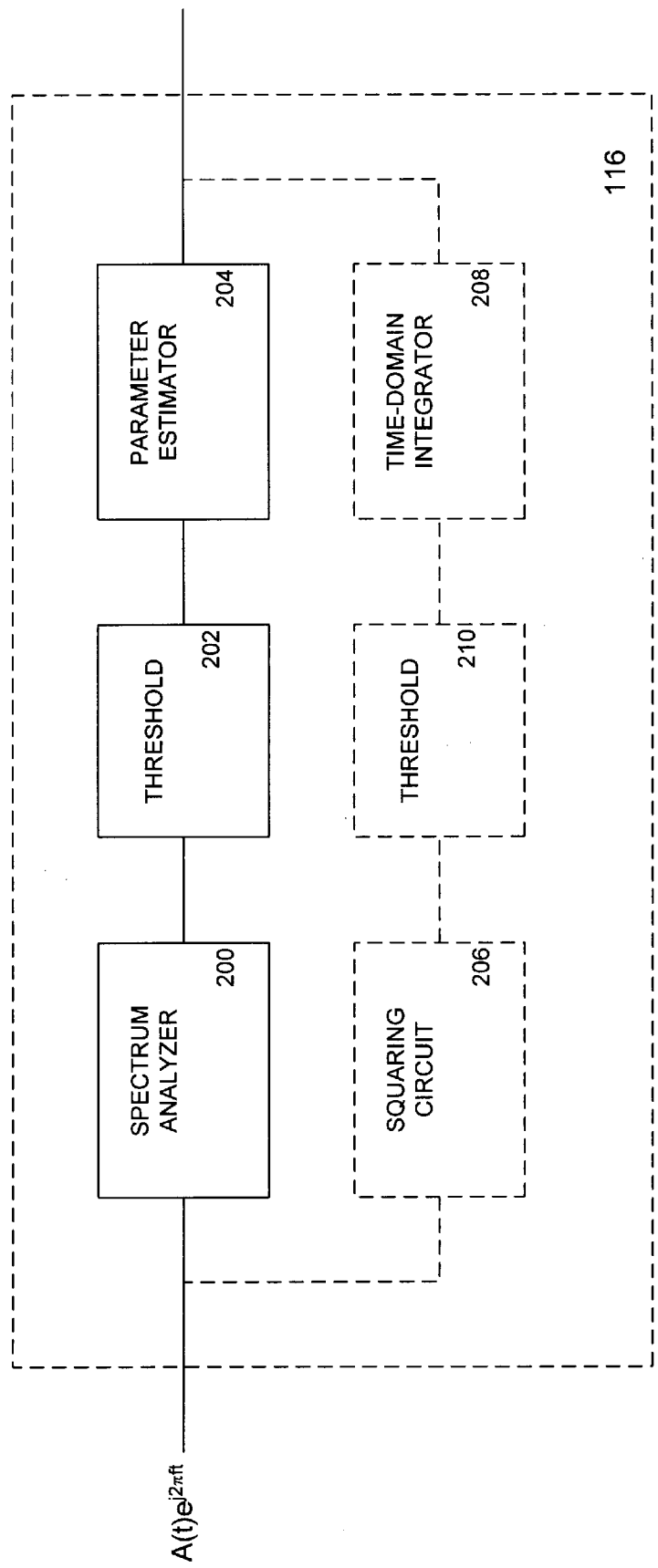
FIG. 2 is a block diagram illustrating digital signal processing circuitry of the present invention.

FIG. 2 is a block diagram illustrating the DSP circuitry 116 of the present invention. For simplicity, the input Doppler signal to the DSP 116 is represented as the continuous time signal $A(t)e^{i2\pi ft}$, having time-varying amplitude $A(t)$ and frequency f. Those skilled in the art will recognize that the actual signal is in discrete-time form and is band-limited, and actually comprises a variety of frequency components of varying amplitudes.

Spectrum analyzer circuitry 200 calculates the Doppler energy spectrum (energy spectral density) of the Doppler frequency shift signal. The spectrum is referred to as an "energy spectral density" herein, rather than the more familiar "power spectral density" because the returning sampled time-limited echoes have finite energy. In any event, the terms are frequently used interchangeably by those skilled in the art.

Thresholding circuitry 202 may be included to eliminate or pass spectral components based upon their amplitude (energy). For example, to enhance imaging of blood, an upper energy threshold may be used to eliminate high-energy tissue reflections. For tissue imaging, a low-energy threshold may be used to eliminate low-energy echoes from blood.

A parameter estimator 204 of the present invention employs the energy density spectrum to calculate a variety of energy-related parameters that are based on energy alone or a combination of energy and velocity. The energy-related function based on the energy alone can be written as $$E(t)=\int S(f,t)df$$

where $S(f,t)$ is the Doppler energy spectrum (i.e., the squared magnitude or intensity spectrum), $E(t)$ is the total energy of the Doppler intensity spectrum $S(f,t)$ at a time t, and f is the Doppler frequency.

In PW mode, this energy is also a measure of the integrated backscatter energy within the range-gate region of interest. In conventional integrated backscatter energy calculations, the B-mode intensity images are integrated over the entire insonified region to obtain the integrated backscatter energy. The principle behind this technique is the assumption that the integrated backscatter energy is an estimate of density of the reflecting medium within the region. In PW mode, the present invention inherently calculates the integrated energy of each returning echo over a gated region using Doppler techniques. Because the target is interrogated multiple times (e.g., 128), multiple energy samples are collected. The energy calculated by this invention is thus the total energy over the interrogation time period. Further, although DTI energy mode imaging also integrates over a range gate, DTI energy mode uses color processing and display techniques. In contrast, the present invention calculates parameters for strip display.

The conventional B-mode calculation of integrated backscatter energy requires complex computations, thereby requiring complicated hardware and software to perform the computations in real time. The DTI energy mode method of obtaining integrated backscatter energy exhibits the slow display frame rate and relatively low signal-to-noise ratio of color display systems.

The present invention overcomes these disadvantages. Unlike B-mode systems, the present invention determines backscatter energy for a single region of interest. This determination is much simpler and more appropriate for clinical applications than B-mode systems that compute energy over the entire insonified region. Further, the calculation of integrated backscatter energy for strip display is much simpler and less costly than DTI color mode, and exhibits much better temporal resolution.

The energy-related function based upon a combination of energy and velocity may be expressed as $$EV(t)=K\int S^m(f,t)f^n df$$

where $EV(t)$ is an energy-velocity product function, and m and n are constants that are either preprogrammed or controllable by a user through a suitable, conventional user interface. K is a constant of proportionality to convert the energy-velocity product function from dependence upon frequency to dependence upon velocity, as derived from the Doppler equation. Of course, the above expressions are actually implemented in discrete form by digital circuitry of the invention.

The constants m and n can be selected to take on any values that have diagnostic utility. In a simple case, m=n=1. For example, setting m=1−n, where m and n are less than 1, may be useful for balancing the effects of the energy and velocity measurements. The user may wish to emphasize the Doppler energy spectrum parameter in the energy-velocity product or measure energy alone if the product parameter is only indicating relatively small values when it is weighted heavily in favor of the velocity. This may occur where the angle between the direction of propagation of the ultrasound signal and the direction of movement of the scatterer is large, e.g., greater than 60 degrees. Alternatively, slow-moving tissue would provide a similar indication. Further, a high volume, low-velocity jet of blood may be better diagnosed with energy alone or an energy-velocity product weighted in favor of the energy spectrum.

Conversely, a thin, high-velocity jet of blood may be better detected with a product parameter emphasizing the velocity component. The advantage of using the product parameter in this instance instead of velocity alone is that the product parameter may give some indication of the volume of the scatterers reflecting the ultrasonic energy.

In general, a relatively high or low product parameter in one region compared to that measured in an adjacent region within the body may provide an initial indication of medical problems. Measurements from nearby regions should be compared relative to one another to account for the effects of angle on the measurements.

Figure 4:
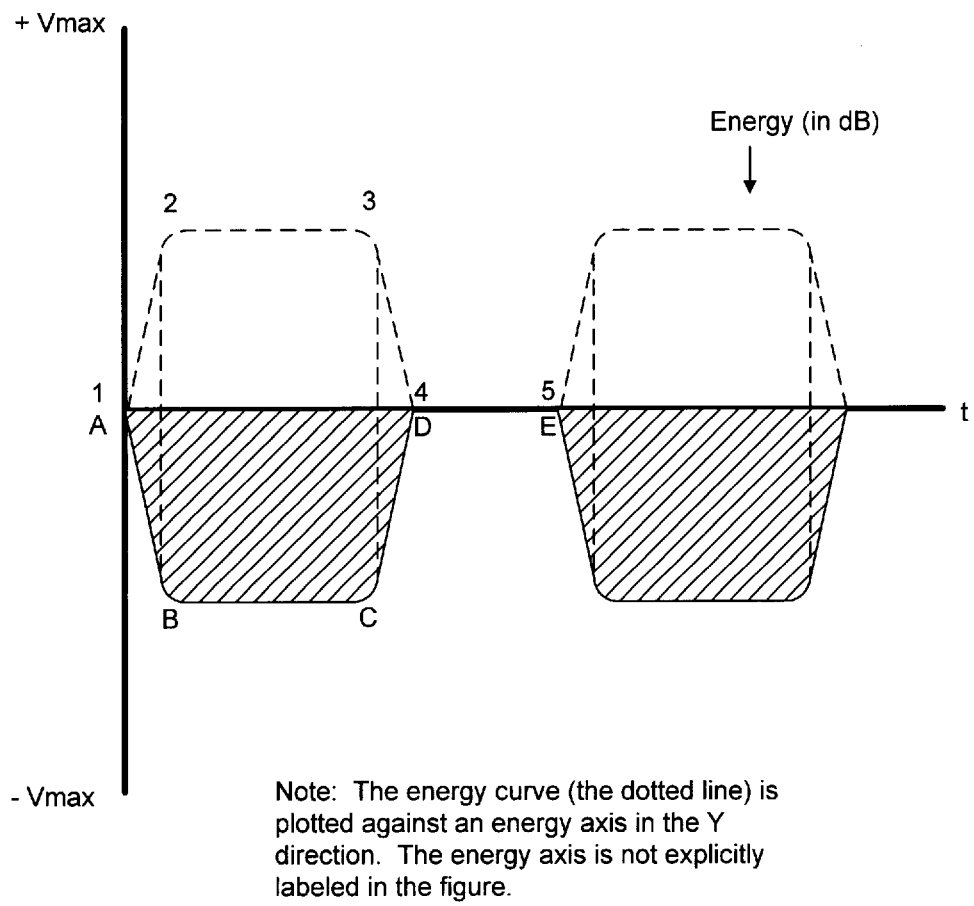
FIG. 4 illustrates an example of a strip Doppler display of velocity and energy according to the present invention.

FIG. 4 illustrates an example of a Doppler strip display of a flow that increases in velocity from point A to point B, stays constant in velocity from B to C and decreases in velocity from C to D. No flow exists from D to E. This cycle repeats. The shaded region indicates that the flow contains its spectral components within the envelope ABCDE. The energy of the flow may look like the dotted curve 12345. From 1 to 2 the energy increases, indicating onset of flow. From 2 to 3 the energy remains constant, indicating constant flow. From 3 to 4 energy decreases, indicating decreasing flow. Finally, no flow is indicated from 4 to 5.

The embodiment described above computes energy and velocity-based functions in the frequency domain. Those skilled in the art will recognize that the DSP circuitry can employ equivalent time-domain techniques to calculate energy alone, thereby bypassing the spectrum analyzer and parameter estimator for the energy calculation. For example, Rayleigh's or Parseval's theorem illustrates the equivalence of calculating energy in the time and frequency domains.

Accordingly, referring to FIG. 2, the DSP 116 includes an optional time-domain energy calculator comprising a squaring circuit 206 and integrator (accumulator) 208 for integrating the squared amplitude of the Doppler signal over time in order to obtain Doppler energy. The time-domain path may also include thresholding circuitry 210 to eliminate or pass time samples based upon their amplitude. Those skilled in the art will recognize that the squaring circuit may be a simple multiplier or employ more sophisticated rectification and filtering techniques known in the art to obtain energy as a function of time. Also, this time-domain energy calculation circuitry can be located elsewhere in the system, as would be easily appreciated by those skilled in the art. Further techniques for calculating Doppler parameters in the time domain are described in U.S. Pat. No. 4,928,698, issued to Bonnefous and Bonnefous, et al., "Time Domain Formulation of Pulse-Doppler Ultrasound and Blood Velocity Estimation by Cross-Correlation," *Ultrasonic Imaging* B, 73–85 (1986). Those references are incorporated by reference herein.

In strip Doppler mode, the spectrum analyzer 200 is employed to compute the distribution of Doppler frequencies at a particular time t. This distribution is necessary to compute and display the distribution of velocities in strip mode. Further, the distribution of frequencies is necessary for calculation of the energy-velocity product according to the present invention. That calculation requires multiplication of the squared magnitude spectrum at each frequency by the frequency component itself, followed by integration over the range of frequencies. Other Doppler display modes, such as the color energy velocity mode described in U.S. patent application Ser. No. 08/367,064 do not contemplate calculating an energy-velocity product in this manner.

Figure 3:
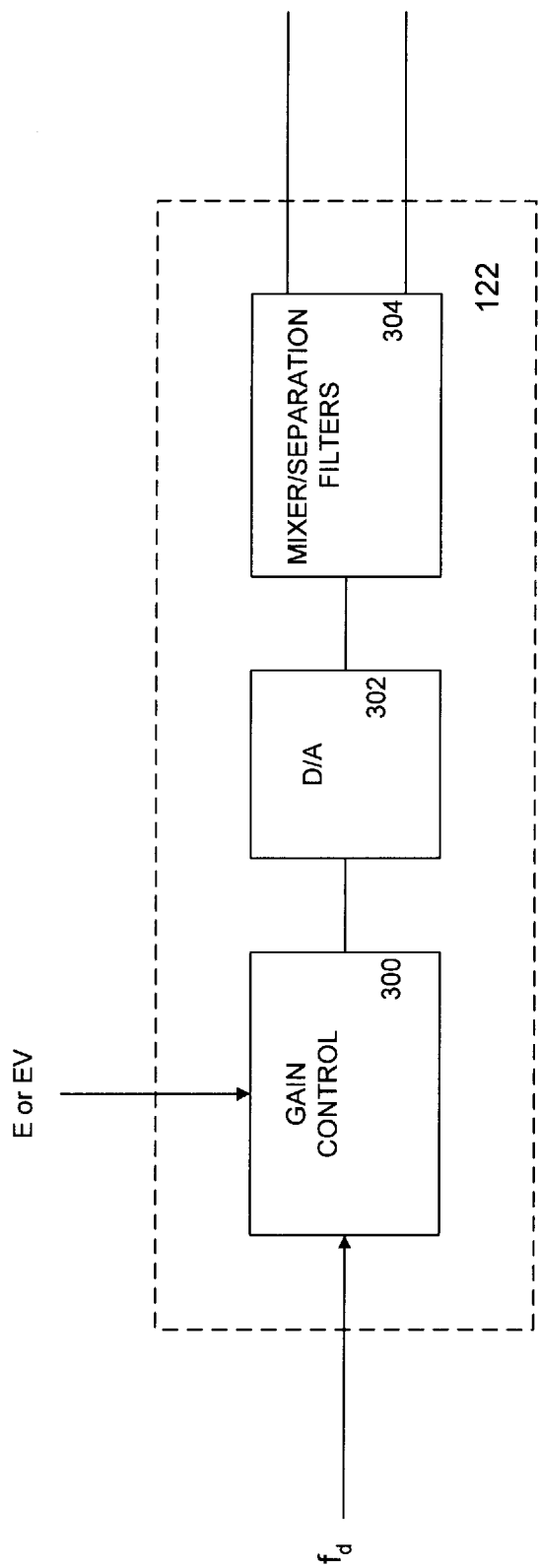
FIG. 3 is a block diagram illustrating one embodiment of an audio processor of the present invention.

As mentioned above, these energy-related parameters are provided to the video processor 118 for display in strip Doppler mode, i.e., the parameters are displayed on the y-axis against time on the x-axis. Strip Doppler has the advantage of a higher frame rate than color flow mode. Parameters are also provided to the audio processor 122 to provide an audio indication of the echo signal. FIG. 3 is a block diagram illustrating one embodiment of the audio processor 122 of the present invention. A gain control circuit 300 receives the Doppler frequency signal and adjusts the gain of the signal based upon the energy-related parameter E or EV received from the DSP circuitry 116. The output is converted back to an analog signal through a digital-to-analog converter (D/A) 302. The analog signal is separated into forward and reverse components by a mixer/separation filter block 304 that provides the forward and reverse components to the speakers 124.

Figure 5:
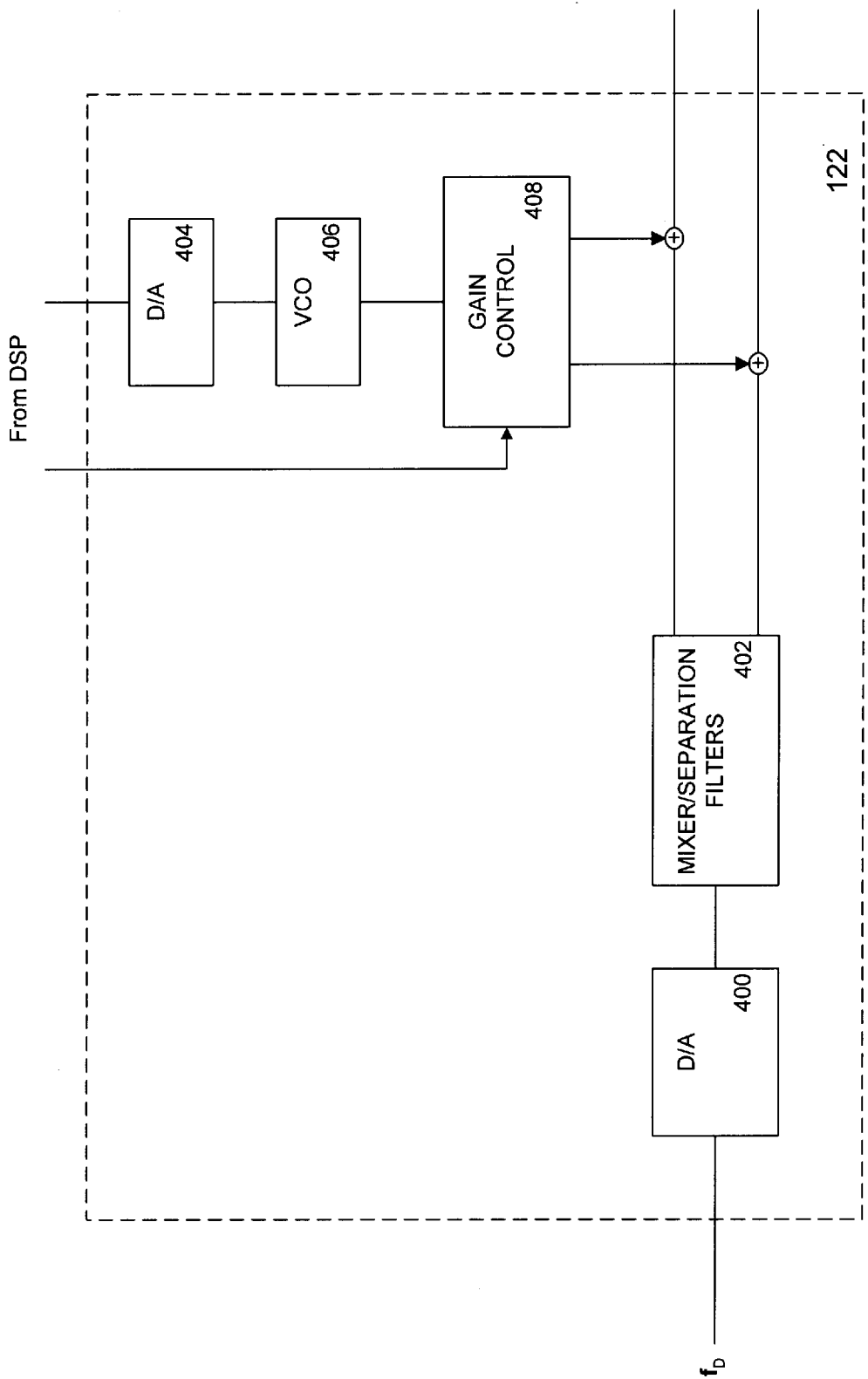
FIG. 5 illustrates an alternative embodiment of an audio processor of the present invention.

FIG. 5 illustrates an alternative embodiment of the audio processor 122 of the present invention. A D/A 400 converts the Doppler frequency signal into analog form. Mixer/separation filters 402 separate the forward and reverse components, as before. In this embodiment, the energy-related parameter controls the frequency and/or gain of a tone that is added to the conventional audio path. The audio processor 122 includes a D/A 404 for converting the energy-related parameter to analog form in order to control the frequency of a tone produced by a voltage controlled oscillator (VCO) 406. The tone is fed into a gain control circuit 408, which may be controlled by the energy-related parameter. The output of the gain stage is added to the forward and reverse audio components.

In this design, through preprogramming or user control, the gain or the frequency of the added tone can be independently controlled, or alternatively controlled at the same time. If only gain is adjusted, then the DSP 116 supplies the energy-related parameter to the gain control 408 while holding the frequency of the VCO 406 constant by supplying a constant signal, instead of an energy-related parameter, to the D/A 404. Alternatively, the D/A 404 and VCO 406 may be eliminated. Conversely, if only frequency is to be modulated, then the DSP 116 will output a constant signal, rather than the energy-related parameter, to the control input of the gain control circuit 408. Alternatively, the gain control may be eliminated.

The audio processing circuitry 122 of the invention provides a number of advantages over conventional systems. For example, sometimes it is difficult to hear the Doppler information inherent in small, low-velocity jets due to the noise of the velocity measurement. In that case, an energy or energy-velocity measurement may provide a better diagnostic indication as the jet volume flow increases and decreases. Further, the use of energy-related information to control the gain and/or frequency of an added tone or the gain of the conventional audio signal provides an intuitive indication of the strength of the echo signal due to the volume of the scanned medium.

Although the invention has been described in conjunction with particular embodiments, it will be appreciated that various modifications and alterations may be made by those skilled in the art without departing from the spirit and scope of the invention. For example, those skilled in the art will recognize that the techniques described herein can easily be modified to apply to continuous and high pulse repetition frequency imaging modes. The invention is not to be limited by the foregoing illustrative details, but rather is to be defined by the appended claims.

What is claimed is:

1. In an ultrasound imaging system having a transducer for transmitting an ultrasound signal into a body and receiving a reflected ultrasound signal, an apparatus for determining energy of the reflected signal from tissue within the body, the apparatus comprising:

signal processing circuitry for determining a Doppler intensity spectrum of the signal reflected from the tissue, wherein the Doppler intensity spectrum represents energy of the tissue-reflected signal; and integration circuitry, operatively coupled to the signal processing circuitry, for integrating the Doppler intensity spectrum over Doppler frequency to determine the energy of the tissue-reflected signal as a function of time for display in strip mode.

2. In an ultrasound imaging system having a transducer for transmitting an ultrasound signal into a body and receiving a reflected ultrasound signal, a method for determining energy of the reflected signal from tissue within the body, the method comprising the steps of:

determining a Doppler intensity spectrum of the signal reflected from the tissue, wherein the Doppler intensity spectrum represents energy of the tissue-reflected signal; and integrating the Doppler intensity spectrum over Doppler frequency to determine the energy of the tissue-reflected signal as a function of time for display in strip mode.

3. In an ultrasound imaging system having a transducer for transmitting an ultrasound signal into a body and receiving a reflected ultrasound signal, an apparatus for determining energy of the reflected signal from tissue within the body, the apparatus comprising:

squaring circuitry for determining the squared amplitude of the tissue-reflected signal; and integration circuitry, operatively coupled to the squaring circuitry, for integrating the squared amplitude in the time-domain to determine the energy of the tissue-reflected signal as a function of time for display in strip mode.

4. In an ultrasound imaging system having a transducer for transmitting an ultrasound signal into a body and receiving a reflected ultrasound signal, a method for determining energy of the reflected signal from tissue within the body, the method comprising the steps of:

determining the squared amplitude of the tissue-reflected signal; and integrating the squared amplitude in the time-domain to determine the energy of the tissue-reflected signal as a function of time for display in strip mode.

5. In an ultrasound imaging system having a transducer for transmitting an ultrasound signal into a body and receiving a reflected ultrasound signal, an apparatus for determining an energy-related function of the reflected signal, the apparatus comprising:

signal processing circuitry for determining a Doppler intensity spectrum of the reflected signal; and integration circuitry, operatively coupled to the signal processing circuitry, for frequency-integrating the product of a first spectral function and a first velocity function to determine the energy-related function as a function of time for display in strip mode, wherein the first spectral function is a function of the Doppler intensity spectrum and the first velocity function is a function of a velocity-related function.

6. The apparatus of claim 5, wherein the first spectral function is the Doppler intensity spectrum raised to a power m, and the first velocity function is the velocity-related function raised to a power n.

7. The apparatus of claim 6, wherein m=1−n and m and n are less than one.

8. The apparatus of claim 6, wherein the values of m and n are set by a user.

9. The apparatus of claim 5, further comprising a filter for filtering out spectral components reflected from tissue.

10. The apparatus of claim 5, further comprising a thresholding circuit for eliminating spectral components having an intensity above an upper threshold intensity so as to eliminate spectral components reflected from tissue.

11. The apparatus of claim 5, further comprising a thresholding circuit for eliminating spectral components having an intensity below a low threshold intensity so as to eliminate spectral components reflected from blood.

12. In an ultrasound imaging system having a transducer for transmitting an ultrasound signal into a body and receiving a reflected ultrasound signal, a method for determining an energy-related function of the reflected signal, the method comprising the steps of:

determining a Doppler intensity spectrum of the reflected signal; and frequency-integrating the product of a first spectral function and a first velocity function to determine the energy-related function as a function of time for display in strip mode, wherein the first spectral function is a function of the Doppler intensity spectrum and the first velocity function is a function of a velocity-related function.

13. The method of claim 12, the integrating step comprising the steps of:

raising the Doppler intensity spectrum to a power m to generate the first spectral function;

raising the velocity-related function to a power n to generate the first velocity function; and integrating the product of the first spectral function and the first velocity function to determine the energy-related function.

14. The method of claim 13, wherein m=1−n and m and n are less than one.

15. The method of claim 13, further comprising the step of a user setting the values of m and n.

16. The method of claim 12, further comprising the step of filtering out spectral components reflected from tissue.

17. The method of claim 12, further comprising the step of eliminating spectral components having an intensity above an upper threshold intensity so as to eliminate spectral components reflected from tissue.

18. The method of claim 12, further comprising the step of eliminating spectral components having an intensity below a lower threshold intensity so as to eliminate spectral components reflected from blood.

19. In an ultrasound imaging system for producing an audio output related to Doppler frequency and having circuitry for determining an energy-related parameter of a reflected ultrasound signal, audio processing circuitry comprising:

tone generation circuitry for generating a tone related to the energy-related parameter; and combining circuitry for combining the tone with the audio output.

20. The audio processing circuitry of claim 19, wherein the tone generation circuitry modulates the frequency of the tone based upon the energy-related parameter, and the combining circuitry adds the tone to the audio output.

21. The audio processing circuitry of claim 19, wherein the tone generation circuitry modulates the amplitude of the tone based upon the energy-related parameter, and the combining circuitry adds the tone to the audio output.

22. The audio processing circuitry of claim 19, wherein the energy-related parameter is energy.

23. The audio processing circuitry of claim 19, wherein the energy-relatedparameter is an energy-velocity product function.

24. In an ultrasound imaging system for producing an audio output related to Doppler frequency and having circuitry for determining an energy-related parameter of a reflected ultrasound signal, a method for audio processing comprising:

generating a tone related to the energy-related parameter; and combining the tone with the audio output.

25. The method of claim 24, wherein the generating step comprises the step of modulating the frequency of the tone based upon the energy-related parameter; and the combining step comprises the step of adding the tone to the audio output.

26. The method of claim 24, wherein:

the generating step comprises the step of modulating the amplitude of the tone based upon the energy-related parameter; and the combining step comprises the step of adding the tone to the audio output.

27. The method of claim 24, wherein the energy-related parameter is energy.

28. The method of claim 24, wherein the energy-related parameter is an energy-velocity product function.

29. In an ultrasound imaging system for producing an audio output related to Doppler frequency, audio processing circuitry comprising:

circuitry for determining an energy-related parameter of a reflected ultrasound signal; and gain control circuitry for controlling the gain of the audio output in response to the energy-related parameter.

30. The audio processing circuitry of claim 29, wherein the energy-related parameter is energy.

31. The audio processing circuitry of claim 29, wherein the energy-related parameter is an energy-velocity product function.

32. In an ultrasound imaging system for producing an audio output related to Doppler frequency, a method for audio processing comprising the steps of:

determining an energy-related parameter of a reflected ultrasound signal; and controlling the gain of the audio output in response to the energy-related parameter.

33. The method of claim 32, wherein the energy-related parameter is energy.

34. The method of claim 32, wherein the energy-related parameter is an energy-velocity product function.

* * * * *